(12) United States Patent
Weber et al.

(10) Patent No.: US 8,202,245 B2
(45) Date of Patent: Jun. 19, 2012

(54) MEDICAL DEVICES AND METHODS OF MAKING THE SAME

(75) Inventors: Jan Weber, Maple Grove, MN (US); Steven M. Spencer, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2277 days.

(21) Appl. No.: 11/045,955

(22) Filed: Jan. 26, 2005

(65) Prior Publication Data

US 2006/0167407 A1 Jul. 27, 2006

(51) Int. Cl.
*A61M 37/00* (2006.01)

(52) U.S. Cl. .................................... 604/103.08

(58) Field of Classification Search ............. 604/103.08
See application file for complete search history.

(56) References Cited

U.S. PATENT DOCUMENTS

| | | | |
|---|---|---|---|
| 3,752,617 A | 8/1973 | Burlis et al. | |
| 4,963,313 A | 10/1990 | Noddin et al. | |
| 5,195,969 A | 3/1993 | Wang et al. | |
| 5,270,086 A | 12/1993 | Hamlin | |
| 5,501,759 A | 3/1996 | Forman | |
| 5,549,117 A * | 8/1996 | Tacklind et al. | 600/529 |
| 5,714,110 A | 2/1998 | Wang et al. | |
| 5,733,301 A | 3/1998 | Forman | |
| 5,737,126 A | 4/1998 | Lawandy | |
| 5,826,588 A * | 10/1998 | Forman | 128/898 |
| 6,010,480 A | 1/2000 | Abele et al. | |
| 6,010,521 A | 1/2000 | Lee et al. | |
| 6,027,477 A | 2/2000 | Kastenhofer | |
| 6,068,634 A | 5/2000 | Lorentzen Cornelius et al. | |
| 6,120,364 A | 9/2000 | Laflamme | |
| 6,129,706 A * | 10/2000 | Janacek | 604/103.08 |
| 6,177,151 B1 | 1/2001 | Chrisey et al. | |
| 6,440,503 B1 | 8/2002 | Merdan et al. | |
| 6,540,672 B1 * | 4/2003 | Simonsen et al. | 600/300 |
| 6,620,191 B1 | 9/2003 | Svensson | |
| 6,740,191 B2 | 5/2004 | Clarke et al. | |
| 7,025,743 B2 * | 4/2006 | Mann et al. | 604/66 |
| 7,374,791 B2 * | 5/2008 | Flanagan | 427/2.24 |
| 2001/0027310 A1 | 10/2001 | Parisi et al. | |
| 2003/0004535 A1 | 1/2003 | Musbach et al. | |

(Continued)

FOREIGN PATENT DOCUMENTS

WO WO 01/32398 A1 5/2001

(Continued)

OTHER PUBLICATIONS

Csete et al., "Application possibilities and chemical origin of submicrometer adhesion modulation on polymer gratings produced by UV laser illumination," Materials Science and Engineering C, Elsevier Science S.A., CH, vol. 26, No. 5-7, pp. 1056-1062, Jul. 2006.

(Continued)

*Primary Examiner* — Nicholas Lucchesi
*Assistant Examiner* — Diva Ranade
(74) *Attorney, Agent, or Firm* — Seager, Tufte & Wickhem, LLC

(57) ABSTRACT

Medical devices and methods of making the devices are described. In some embodiments, a method of making a medical device includes addressing a member including a polymer with energy above an ablation threshold of the polymer, and using the member to make the medical device.

14 Claims, 3 Drawing Sheets

U.S. PATENT DOCUMENTS

| | | | |
|---|---|---|---|
| 2003/0028243 A1 | 2/2003 | Bates et al. | |
| 2003/0060832 A1 | 3/2003 | Guinan et al. | |
| 2003/0125762 A1* | 7/2003 | Eidenschink | 606/194 |
| 2004/0086674 A1 | 5/2004 | Holman | |
| 2004/0106973 A1 | 6/2004 | Johnson | |
| 2004/0215492 A1* | 10/2004 | Choi | 705/2 |
| 2004/0243043 A1 | 12/2004 | McCarthy et al. | |
| 2005/0154271 A1* | 7/2005 | Rasdal et al. | 600/347 |
| 2007/0142822 A1* | 6/2007 | Remde | 604/890.1 |

FOREIGN PATENT DOCUMENTS

| | | |
|---|---|---|
| WO | WO 02/056930 A3 | 7/2002 |
| WO | 2004/041344 | 5/2004 |
| WO | 2006/065356 | 6/2006 |
| WO | 2006/081419 | 8/2006 |

OTHER PUBLICATIONS

Dadsetan, et al., "In vitro studies of platelet adhesion on laser-treated polyethylene terephatalate surface," J. Biomed.Mat.Res., vol. 54, 2001, pp. 540-546.

Fewster, "Precise ultrafine surface texturing of implant materials to improve cellular adhesion and biocompatibility," Nanobiology, vol. 3, pp. 201-210, (1994).

Hunt, "Laser surface modification of polymers to improce biocompatibility," Journal of Materials Science in Medicine, vol. 6, pp. 813-817, (1995).

Mayer et al., "Physico-chemical and biological evaluation of excimer laser irradiated polyethylene terephthalate (pet) surfaces," Biomaterials, Elsevier Science Publishers BV., Barking, GB, vol. 27, No. 4, pp. 553-566, Feb. 2006.

Yip et al., "Study of plasma-etched and laser-irradiated polyamide materials," Mat. Res. Innovation, vol. 6, pp. 44-50, (2002).

J. Yip et al., "Study of plasma-etched and laser-irradiated polyamide materials," Mat Res Innovat (2002) 6:44-50.

William Bertolino et al., "Medical Balloon," U.S. Appl. No. 10/263,225, filed Oct. 2, 2002.

Paul DiCarlo et al., "Embolic Compositions," U.S. Appl. No. 10/791,103, filed Mar. 2, 2004.

* cited by examiner

MEDICAL DEVICES AND METHODS OF MAKING THE SAME

TECHNICAL FIELD

The invention relates to medical devices and methods of making the same.

BACKGROUND

A balloon catheter is a medical device that includes an inflatable balloon carried by a elongated catheter shaft. The balloon catheter can be used to administer a variety of treatments. For example, in an angioplasty procedure, the balloon can be inflated to widen a constricted bodily vessel, such as a coronary artery. The balloon catheter can also be used to deliver a tubular member, such as an endoprosthesis (e.g., a stent), that is placed in the body to reinforce or to reopen a blocked vessel.

In angioplasty, the balloon can be used to treat a stenosis, or a narrowing of the bodily vessel, by collapsing the balloon and delivering it to a region of the vessel that has been narrowed to such a degree that blood flow is restricted. The balloon can be delivered to a target site by passing the catheter over an emplaced guidewire and advancing the catheter to the site. In some cases, the path to the site can be rather tortuous and/or narrow. Upon reaching the site, the balloon is then expanded, e.g., by injecting a fluid into the interior of the balloon. Expanding the balloon can expand the stenosis radially so that the vessel can permit an acceptable rate of blood flow. After use, the balloon is collapsed and withdrawn.

In stent delivery, the stent is compacted on the balloon and transported to a target site. The stent can include a metallic tubular member, and in some cases, the stent can include a polymeric graft material to form a covered stent or a stent-graft. Upon reaching the site, the balloon can be expanded to deform and to fix the stent at a predetermined position, e.g., in contact with the vessel wall. The balloon can then be collapsed and withdrawn.

SUMMARY

The invention relates to medical devices and methods of making the same.

In one aspect, the invention features selectively forming one ore more textured surfaces on one or more components of a medical device. The textured surface can include ripple-like fibers that strengthens or reinforces the component, while providing good flexibility. In some embodiments, the textured surface can be used to deposit one or more drugs in a predetermined sequence. The textured surface(s) can be formed by laser treatment at high fluence and/or by plasma treatment.

In another aspect, the invention features a method of making a medical device, including addressing a member having a polymer with energy above an ablation threshold of the polymer, and using the member to make the medical device.

Embodiments may include one or more of following features. The energy has a fluence greater than about 40 mJ/cm$^2$. The energy is delivered from a laser. The method further includes pulsing the energy delivered from the laser. The addressed member is textured and includes a raised portion having a height of about 0.5 micron. The member is a tubular member. The medical device includes a medical balloon. The tubular member includes a plurality of layers. The method further includes forming a first polymeric layer on the tubular member. The method further includes forming the tubular member into a catheter. The addressed member includes a first portion and a second portion raised relative to the first portion, and the method further includes placing a first therapeutic agent on the first portion, and placing a second therapeutic agent on the second portion. The medical device is a medical graft. The medical device is an endoprosthesis.

In another aspect, the invention features a method of making a medical device, including addressing a member having a polymer with laser energy having a fluence greater than an ablation threshold of the polymer, the laser energy producing a surface on the member having a first portion and a second portion raised relative to the first portion, and using the member to make the medical device.

Embodiments may include one or more of following features. The laser energy is delivered from an excimer laser. The energy has a fluence greater than about 40 mJ/cm$^2$. The method further includes pulsing the energy. The second portion has a height of about 0.5 micron. The member is a tubular member. The medical device comprises a medical balloon. The tubular member includes a plurality of layers. The method further includes forming a first polymeric layer on the tubular member. The method further includes forming the tubular member into a catheter. The method further includes placing a first therapeutic agent on the first portion, and placing a second therapeutic agent on the second portion. The medical device includes a medical graft. The medical device includes an endoprosthesis.

In another aspect, the invention features a medical device, including a surface having a plurality of first portions and a plurality of second portions raised relative to the first portions, the second portions having an average height of about 0.1 to about three microns.

Embodiments may include one or more of following features. The surface is an outer surface. The surface is an interfacial surface between two layers of the medical device. The device further includes a first therapeutic agent on the first portions, and a second therapeutic agent on the second portions. The device is in the form of a medical graft. The device includes a tubular member having the surface, wherein the second portions extend generally transverse to a longitudinal axis of the tubular member. The device is in the form of the medical balloon. The device is in the form of a catheter. The device is in the form of a medical graft. The device is in the form of an endoprosthesis. The device includes a member comprising a polymer, the member defining the surface.

In another aspect, the invention features a method of making a medical device, including contacting a member having a polymer with a plasma to produce a surface on the member a plurality of first portions and a plurality of second portions raised relative to the first portions; and using the member to make the medical device.

Embodiments may include one or more of following features. The plasma includes oxygen and/or argon. The method includes contacting the member with the plasma at less than about 25° C. The second portions have a height less than about a micron. The member includes a polymer. The method further includes placing a first therapeutic agent on the first portions, and placing a second therapeutic agent on the second portions. The medical device is selected from the group consisting of a medical balloon, a catheter, an endoprosthesis, and a medical graft.

Other aspects, features, and advantages will be apparent from the description of the embodiments thereof and from the claims.

DETAILED DESCRIPTION

Figure 1:
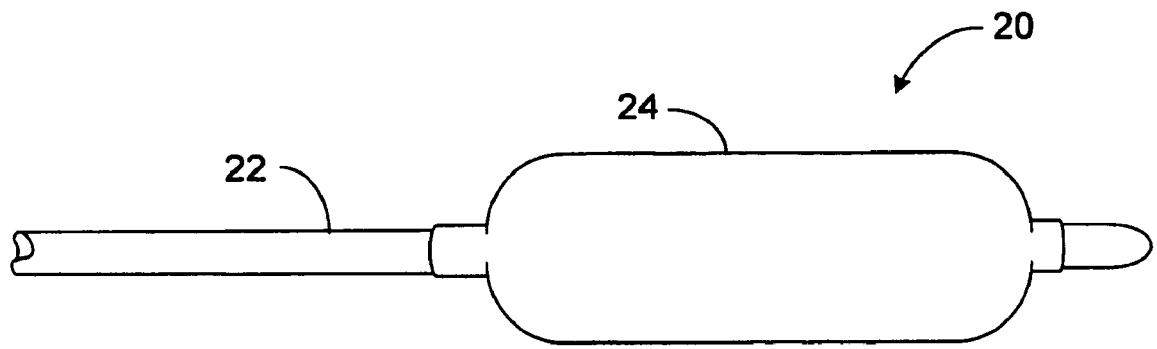
FIG. 1 is a perspective illustration of an embodiment of a balloon catheter.
Figure 2:
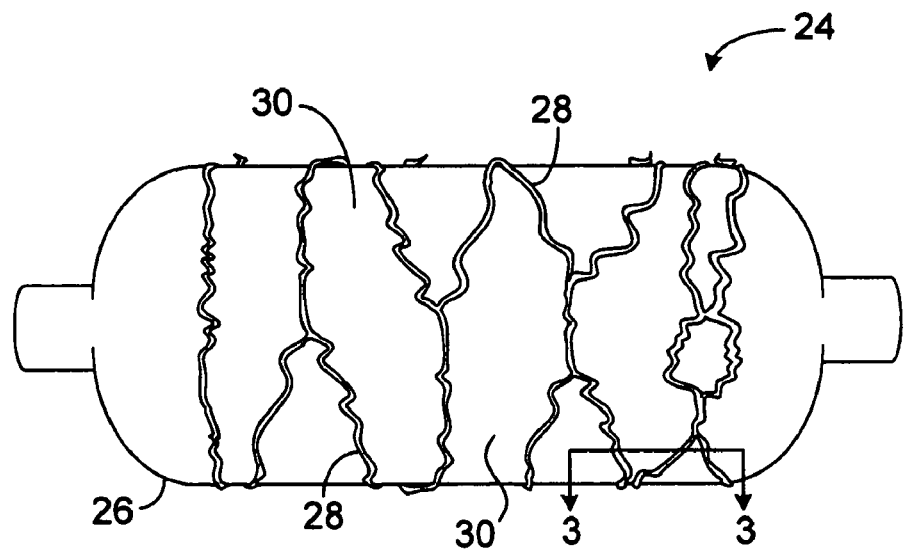
FIG. 2 is a detailed illustration of the balloon catheter of FIG. 1.
Figure 3:
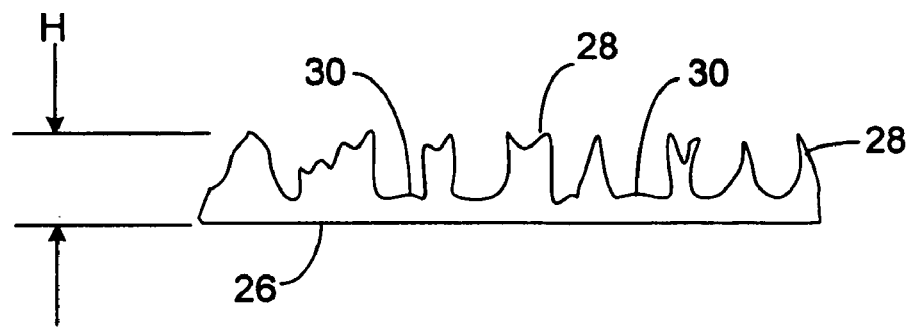
FIG. 3 is a detailed, cross-sectional illustration of the balloon of FIG. 2, taken along line 2-2.

Referring to FIG. 1, a balloon catheter 20 includes a catheter shaft 22 and an inflatable balloon 24 carried by the shaft. Referring also to FIGS. 2 and 3, balloon 24 is a polymeric body 26 that includes a textured outer surface having raised portions 28 and relatively recessed portions 30. As shown, raised portions 28 are fiber-like and/or ripple-like structures that extend circumferentially and somewhat periodically about balloon 24. Together, raised portions 28 and recess portions 30 are capable of enhancing the strength of balloon 24 (e.g., increasing the burst strength of the balloon) while providing good flexibility so that the balloon can track a tortuous bodily vessel.

The textured surface of balloon 24 can be formed by laser treating the surface of the balloon. The total photonic energy that is delivered to the surface can determine the morphology of the surface, with increasing power and treatment time producing more distinct ripple-like structures. For example, the mean distance between raised portions 28 can increase with increasing number of laser pulses applied and with increasing laser fluence. Also, increasing the number of laser pulses can result in a coarser structure, which may be due to earlier formed raised portions merging together. Without wanting to be bound by theory, it is believed that the formation of raised portions 28 is likely due to the melting of the top surface of the addressed material as a result of a hot plasma that is created during a high fluence laser pulse. The plasma may also create a high local pressure that is pushing out the molten material from underneath the plasma. At low fluence levels (e.g., below the ablation threshold described below), there may be no plasma, and therefore, no melting and no creation of ripples.

The total energy can be delivered by increasing power and decreasing treatment time, or by decreasing power and increasing treatment time. In some embodiments, balloon 24 can be addressed with high laser energy by using an ultraviolet excimer laser (such as a Lambda Physik COMP EX 205 laser operating with ArF gas, at 193 nm). The laser fluence that is used is a function of the addressed material (e.g., its absorption properties) and is above the ablation threshold of the material. As used herein, the ablation threshold of a material is the lowest energy level at which chemical bonds of the material are broken (e.g., due to thermal and/or photochemical effects), and a portion (e.g., a layer) of the material is vaporized. The laser fluence can range from about 40 mJ/cm$^2$ to about 5000 mJ/cm$^2$. In some embodiments, the laser fluence can be up to about 100 times greater than the ablation threshold of the material; for example, a material having an ablation threshold of 50 mJ/cm$^2$ can be addressed with energies from about 50 to about 5000 mJ/cm$^2$. In some embodiments, the laser energy can be pulsed (e.g., at 1 Hz) to form the textured surface. Similarly, treatment times can also be a function of the addressed materials and fluence that is applied to the material. For example, for a material including a polyamide (such as Nylon 12), a laser fluence of about 150 mJ/cm$^2$ and a treatment including 10 pulses (each 20 nanoseconds) for a total energy of 1500 mJ/cm$^2$ can be used; and for a material including polyethylene terephthalate a total energy of about 300 mJ/cm$^2$ can be used. Laser treatment of polymer materials is also described in Yip et al., *Mat. Res. Innovat.* (2002) 6:44-50, hereby incorporated by reference.

Referring particularly to FIG. 3, raised portions 28 have a height, H, on the order of microns. In some embodiments, raised portions 28 have an average height of less than about three microns (e.g., from about 0.1 micron to about three microns). The average height can be greater than or equal to about 0.1 micron, about 0.5 micron, about one micron, or about two microns; and/or less than or equal to about three microns, about two microns, about one micron, or about 0.5 micron. A medical device, such as balloon 24, can have raised portions 28 of generally the same height, or different portions of the medical device, such as body 26, can have raised portions of different heights.

Figure 4:
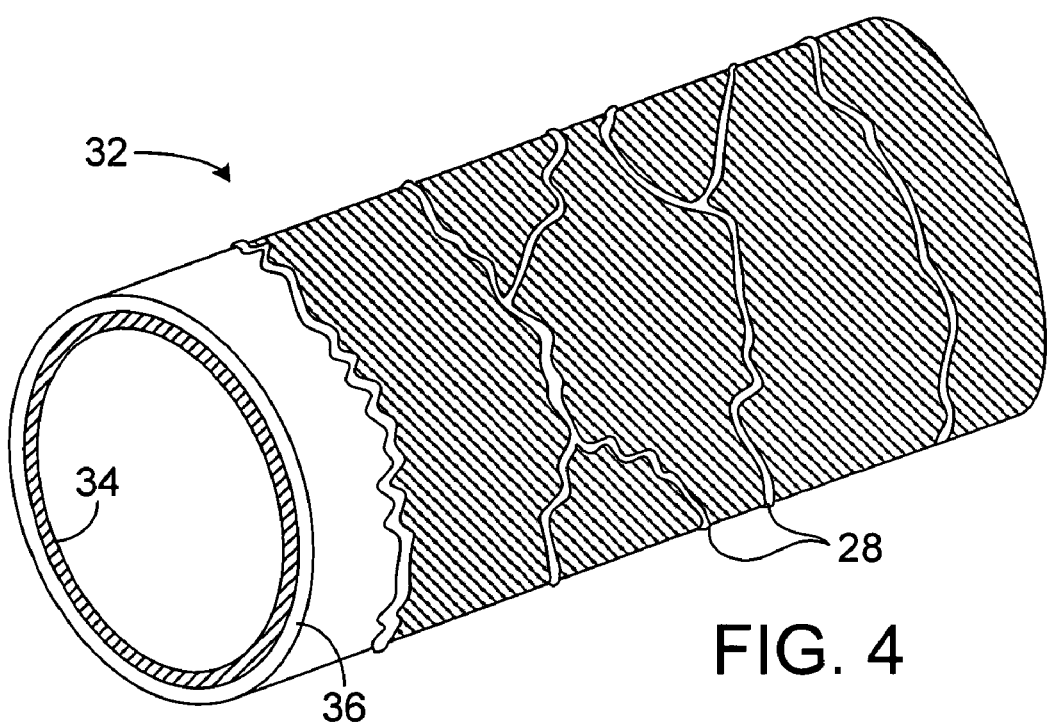
FIG. 4 is partial, perspective illustration of an embodiment of a balloon.

Body 26 of balloon 24 can be formed of a single homogenous layer as shown in FIG. 3, or in other embodiments, body 26 can include a plurality of layers. As shown in FIG. 4, a balloon 32 includes an inner layer 34 and an outer layer 36, which can include a material that is harder or softer than the material of the inner layer. For example, inner layer 34 can be formed of a relatively soft polymer, and outer layer 36 can be formed of a relatively hard polymer. Outer layer 36 can be laser treated to form ripple-like raised portions 28 and recessed portions 30 such that the harder outer layer can reinforce inner layer 34, and the strength of balloon 32 can be enhanced. At the same time, relatively soft inner layer 34 can provide balloon 32 with good flexibility and trackability. As shown in FIG. 4, a laser treated layer (as shown, outer layer 36) can be laser treated so as to reveal portions of an adjacent layer (as shown, underlying inner layer 34), or a layer can be laser treated, similar to body 26 shown in FIG. 3, such that portions of the adjacent layer is not revealed. A medical device can have one or more portions in which a laser treated layer reveals an adjacent layer, and/or one or more portions in which the laser treated layer does not reveal the adjacent layer.

Figure 5:
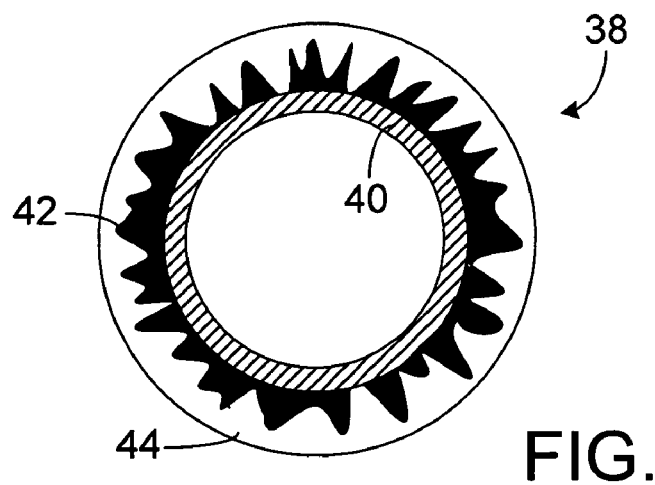
FIG. 5 is a cross-sectional view of a multilayered structure.

In some embodiments, the laser treated surface can be an interface between two layers of material. Referring to FIG. 5, a multilayered structure 38, such as a body of a balloon, includes an inner layer 40, an intermediate layer 42, and an outer layer 44. As shown, intermediate layer 42 is laser treated to form raised ripple-like portions, similar to balloon 32, and outer layer 44 is disposed on the intermediate layer. The ripple-like portions can enhance the overall strength of structure 38, and at the same time, the bonding between intermediate layer 42 and outer layer 44 can be enhanced because of an increase in surface area. As a result, multilayered structure 38 can be less susceptible to delamination. In other embodiments, more than one layer of a multilayered structure can be laser treated. Alternatively or additionally to intermediate layer 42, inner layer 40 and/or outer layer 44 can be laser treated to form ripple-like structures, in any combination. For example, an inner layer and a middle layer can be laser ablated to form an open fiber network that partly exposes the inner layer. After ablation, applying a third layer (for example, made of the same material of the inner layer) that adheres well to the inner layer can strongly embed the fiber network.

Embodiments of the balloons described above can be formed by laser treating the balloon or a tube or parison from which the balloon is made. For example, a monolayer or multilayer tube can be prepared by an extrusion process. Generally, this process can involve the use of an extrusion apparatus (e.g., a crosshead, such as a compact crosshead) having a series of discs. A suitable extrusion apparatus, including some illustrative operating conditions, such as zone heating temperatures, polymer concentrations, feed rate, and line speed, are described in PCT/US01/40220. An exemplary system for controlling the feed rate or flow of polymers, including melt pumps, and systems and methods for controlling the pumps, is also described in WO 01/32398, entitled "Method and Apparatus for Extruding Catheter Tubing". Other methods include using servo-controlled valves, as described in Burlis et al., U.S. Pat. No. 3,752,617.

Exemplary polymer materials for the tube include polymers capable of being crystalline, such as thermoplastics. Examples of thermoplastics include, for example, polyolefins, polyamides, such as nylon 12, nylon 11, nylon 6/12, nylon 6, and nylon 66, polyesters (e.g., PET), polyethers, polyurethanes, polyureas, polyvinyls, polyacrylics, fluoropolymers, copolymers and block copolymers thereof, such as block copolymers of polyether and polyamide, e.g., Pebax®; and mixtures thereof. Other materials are described in PCT/US01/40220.

The tube can then be laser treated as described herein to form raised features. In embodiments in which the laser treated surface will be an interfacial surface, one or more layers of materials can be overmolded on the laser treated surface.

Next, to form a balloon, the formed (e.g., co-extruded) tube can be blow molded. In some embodiments, the tube is placed (e.g., centered) in a preheated balloon mold, and air is introduced into the tube to maintain the patency of the tube lumen. In some embodiments, after soaking at a predetermined temperature and time, the tube is stretched for a predetermined distance at a predetermined time, rate, and temperature. The pressure inside the tube is then sufficiently increased to radially expand the tube inside the mold to form the balloon. Alternatively or additionally to laser treating the tube, the formed balloon can then be laser treated as described herein to form raised features. The formed balloon can be heat treated, for example, to enhance folding memory, and/or folded into a predetermined profile.

Methods of forming a balloon from a tube and using a balloon are described in, for example, commonly-assigned U.S. Ser. No. 10/263,225, filed Oct. 2, 2002, and entitled "Medical Balloon"; Anderson U.S. Pat. No. 6,120,364; Wang U.S. Pat. No. 5,714,110; and Noddin U.S. Pat. No. 4,963,313, all hereby incorporated by reference in their entirety. Other balloon catheter systems are described in, for example, Wang U.S. Pat. No. 5,195,969; and Hamlin U.S. Pat. No. 5,270,086.

While a number of embodiments have been described above, the invention is not so limited.

For example, ripple-like raised portions can be formed by treating one or more components of a medical device with a low temperature (e.g., 20° C.) plasma. Selected portion(s) of the component(s) can be treated by masking portion(s) that are not to be treated. Plasma treatment can be performed using a glow discharge generator (such as SPP-001, Showa Company of Japan), and oxygen and argon as the plasma gases. In some embodiments, up to about 200 Watts of power can be delivered for up to about 30 minutes. Plasma treatment is further described in Yip et al., *Mat. Res. Innovat.* (2002) 6:44-50.

The ripple-like raised portions can be formed on other medical devices. In some embodiments, the medical device can be an endoprosthesis, such as a vascular graft, a stent-graft, or a covered stent, having a polymeric body, e.g., a polymeric tubular body. The polymeric body can be mono-layered or multilayered, and one or more layers can be treated as described herein to form raised portions. As described above, the treated layer(s) can be an outer layer and/or an interfacial layer.

Figure 6:
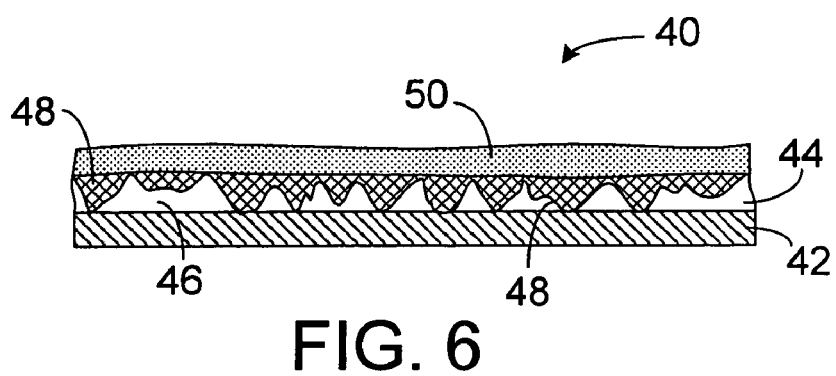
FIG. 6 is a cross-sectional illustration of an embodiment of a medical device.

In embodiments in which an outer layer is treated, one or more drugs or therapeutic agents can be placed on the layer. Referring to FIG. 6, a multilayered structure 40 includes a first layer 42 and a second layer 44, which is on the first layer. As shown, second layer 44 includes ripple-like fibers 46. Multilayered structure 40 further includes a first drug or therapeutic agent 48 placed in the recessed portions of second layer 44, and a second drug or therapeutic agent 50 placed on the first drug. This layering of the drugs allows the drugs to be delivered in a predetermined sequence. As shown FIG. 6, second drug 50 is formed to be delivered before first drug 48 is delivered. In some embodiments, second drug 50 includes an antithrombogenic agent, such as heparin, to reduce any inflammatory responses after implantation into the body, and first drug 48 includes an endothelium stimulant and/or smooth muscle cell inhibitor, such as paclitaxel or taxol. Other drugs and therapeutic agents are described in U.S. Ser. No. 10/791,103, filed Mar. 2, 2004. Drugs 48 and 50 can be applied by any suitable method, for example, by dip coating or spray coating, and excess material can be removed by blading. As another example, drug 48 can be applied with pad printing using a low viscosity fluid, and drug 50 can be applied with pad printing using a high viscosity fluid. Drugs 48 and 50 can be applied, for example, to an endoprosthesis, such as a vascular graft, a stent-graft, or a covered stent, having a polymeric body, or an inflatable balloon.

Figure 7:
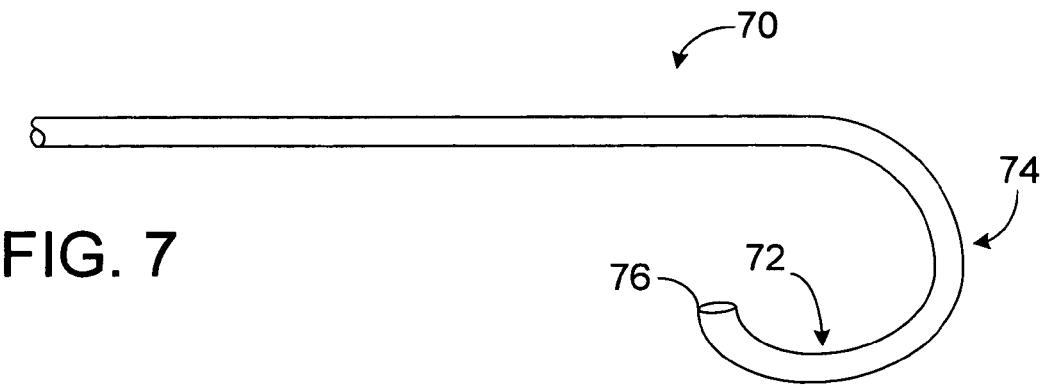
FIG. 7 is an illustration of an embodiment of a catheter.
Figure 8A:
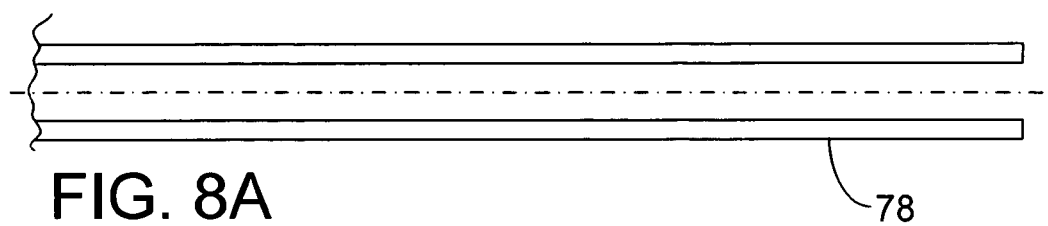
FIGS. 8A, 8B, and 8C illustrate an embodiment of a method of making the catheter of FIG. 7.
Figure 8B:
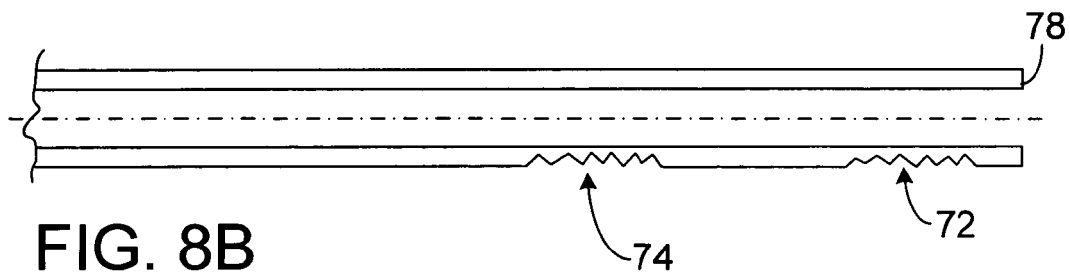
Figure 8C:
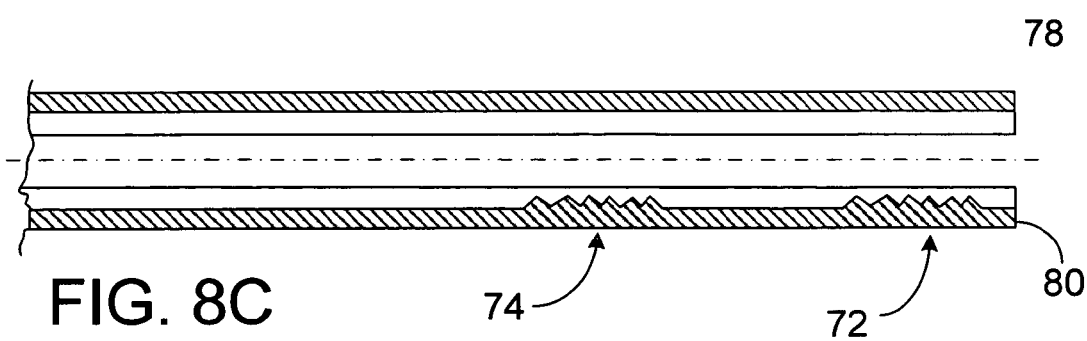

Laser treatment and/or plasma treatment can also be used to provide predetermined and selective flexibility to a medical device. Referring to FIG. 7, a catheter 70, such as a microcatheter used to deliver an aneurysm coil or occlusive device, includes a first curved portion 72 and a second curved portion 74. Portions 72 and 74 can be used, for example, to facilitate introduction of the distal tip of catheter 76 into an aneurysmal sac to deliver the occlusive device. FIGS. 8A-8C show a method of making catheter 70. As shown, catheter 70 is formed from a bilayer tube having a first layer 78 and a second layer 80. First layer 78 is treated at portions corresponding to portions 72 and 74 to form fiber-like structures as described above (FIG. 8B). Second layer 80 is then formed on the treated first layer 78, for example, by overmolding or dipping. In embodiments in which second layer 80 is formed of a material softer than the material of first layer 78, portions 72 and 74 are relatively softer than portions of the bilayer tube that has not been treated. As a result, portions 72 and 74 are relatively more flexible than the untreated portions. In other embodiments, second layer 80 is formed of a material harder than the material of first layer 78, e.g., to stiffen portions 72 and 74. In some embodiments, laser treatment and/or plasma treatment can be used to provide a variable stiffness tube or catheter. For example, relative to a proximal portion of a catheter, the distal portion of the catheter can be more laser treated and can include more softer material to provide greater flexibility at the distal portion for good trackability. Alternatively or additionally, laser treatment can be used to reduce wall thickness at the distal portion to enhance flexibility.

In other embodiments, while FIG. 2 shows raised portions 28 extending circumferentially about balloon 24, the raised portions can extend in other directions. For example, raised portions 28 can extend generally helically about or generally parallel to the longitudinal axis or length of a medical device, which may provide additional structure for controlling (e.g., minimizing) shrinkage and/or growth of the balloon.

Laser treatment and plasma treatment can be selectively applied to any portions of a medical device, and need not be applied to the entire device. For example, the body portion of a balloon, which can be thinner than the cone portions or the waist portions of the balloon, can be selectively treated to reinforce the body portion, while the cone portions and the waist portions can be untreated.

In some embodiments, the ripple-like raised portions may have a different composition than the structure (such as a substrate) adjacent to the raised portions. For example, a two-layer structure can include a bottom layer and a top layer, and the ablation threshold of the top layer may be lower than the ablation threshold of the bottom layer. By applying laser energy having a fluence level intermediate the two ablation thresholds, the top layer can be ablated to create a plasma that will heat and form ripples on the bottom layer without ablating the bottom layer. For example, at 248 nm, polyamide has a threshold of 0.75 J/cm$^2$ and polycarbonate of 0.12 J/cm$^2$. By having a polyamide bottom layer and a polycarbonate top layer, and applying laser energy at a fluence level at, for example, 0.5 J/cm$^2$ to the top layer, the polycarbonate top layer can be ablated to form ripple-like raised portions, thereby modifying the surface morphology of the polyamide bottom layer without removing the polyamide bottom layer. In this example, the raised portions include polycarbonate, while the structure adjacent to the raised portions include polyamide.

The following example is illustrative and not intended to be limiting.

EXAMPLE

A monolayer tube of polyamide 12 (Nylon 12 (PA 12), molding and extrusion compound, Elf Atochem) was wire-extruded (ID 1.4667 mm, OD 1.567 mm, and 50 micrometer wall thickness). The extrusion was run at 195° C. over a copper mandrel. A laser (Lambda Physik, LXPro 210) with KrF (wavelength at 248 nm) was used with a rectangular beam geometry of 13 times 2 mm. A single quartz lens (f=103 mm convex-convex) projected the laser beam at a 1:1 ratio on the tube to give a fluence level of about 156 mJ/cm$^2$. Positioned just before the tube, a stainless steel mask was positioned with a 5 mm by 2 mm long window. Twenty-five pulses, each of 30 nanoseconds, were delivered to an area 5 mm piece on one side of the circumference of the tube. An average of 35 micrometer was ablated during this process, producing ripples of 2 micrometers. The extruded tube on the copper mandrel was unwound from one spool to another spool while repeating this process every two meters. The resulted spool was fed back into the extruder where a second layer (100 micrometer layer thickness) was extruded on top of the first layer. The second layer included soft Pebax 33D, and the extrusion temperature was 150° C. Final tube dimensions were ID=1.4667 mm and OD 1.677 mm.

All publications, applications, patents, and references referred to in this application are herein incorporated by reference in their entirety.

Other embodiments are within the claims.

What is claimed is:

1. A method of preparing a medical balloon, comprising:
   providing a medical balloon having an inner layer formed from a relatively soft polymer and having an outer layer formed from a relatively hard polymer; and
   exposing portions of the outer layer to light from an excimer laser, the light having a fluence between 1 and 100 times larger than an ablation threshold of the outer layer, the exposed portions forming a plurality of ripple-like raised portions and recessed portions that strengthen the outer layer.

2. The method of claim 1, wherein the exposed portions of the outer layer extend circumferentially around the medical balloon.

3. The method of claim 1, wherein the exposed portions of the outer layer extend generally helically around the medical balloon.

4. The method of claim 1, wherein the exposed portions of the outer layer extend generally parallel to a longitudinal axis of the medical balloon.

5. The method of claim 1, further comprising: placing one or more drugs on the exposed portions of the outer layer.

6. The method of claim 1, further comprising:
   exposing additional portions of the outer layer to the light from the excimer laser, the additionally exposed portions being ablated and revealing the inner layer.

7. The method of claim 1, further comprising: placing a first drug in the recessed portions of the outer layer.

8. The method of claim 7, further comprising:
   placing a second drug on the first drug, so that the second drug is deliverable before the first drug.

9. A method of preparing a medical balloon, comprising:
   providing a medical balloon having an inner layer and an intermediate layer, the medical balloon being capable of receiving an outer layer over the intermediate layer;
   exposing portions of the intermediate layer to light from an excimer laser, the light having a fluence between 1 and 100 times larger than an ablation threshold of the intermediate layer, the exposed portions form a plurality of ripple-like raised portions and recessed portions that enhance a bonding ability of the intermediate layer; and
   bonding an outer layer over the intermediate layer.

10. The method of claim 9, further comprising:
    exposing additional portions of the intermediate layer to the light from the excimer laser, the additionally exposed portions being ablated and revealing the inner layer.

11. The method of claim 10, wherein the regions of the intermediate layer that are not additionally exposed form a fiber network.

12. The method of claim 11, wherein the outer layer is made of the same material as the inner layer.

13. The method of claim 9, further comprising: placing a first drug in the recessed portions of the intermediate layer.

14. The method of claim 13, further comprising:
    placing a second drug on the first drug, so that the second drug is deliverable before the first drug.

* * * * *